US009657240B2

(12) United States Patent
Wagner et al.

(10) Patent No.: US 9,657,240 B2
(45) Date of Patent: May 23, 2017

(54) METHOD FOR IMPROVING THE TRANSPORTABILITY OF HEAVY CRUDE OIL

(71) Applicants: Ulrich Wagner, Bernburg (DE); Wolff Balthasar, Ratingen (DE); Dierk Müller, Karben (DE)

(72) Inventors: Ulrich Wagner, Bernburg (DE); Wolff Balthasar, Ratingen (DE); Dierk Müller, Karben (DE)

( * ) Notice: Subject to any disclaimer, the term of this patent is extended or adjusted under 35 U.S.C. 154(b) by 113 days.

(21) Appl. No.: 14/425,431

(22) PCT Filed: Aug. 22, 2013

(86) PCT No.: PCT/DE2013/100302
§ 371 (c)(1),
(2) Date: Mar. 3, 2015

(87) PCT Pub. No.: WO2014/036994
PCT Pub. Date: Mar. 13, 2014

(65) Prior Publication Data
US 2015/0232767 A1    Aug. 20, 2015

(30) Foreign Application Priority Data

Sep. 4, 2012    (WO) ................ PCT/DE2012/100262

(51) Int. Cl.
*C10G 71/00* (2006.01)
*C10G 3/00* (2006.01)
(52) U.S. Cl.
CPC ............... *C10G 71/00* (2013.01); *C10G 3/00* (2013.01)
(58) Field of Classification Search
None
See application file for complete search history.

(56) References Cited

U.S. PATENT DOCUMENTS 3,870,063 A    3/1975    Hayward
4,027,688 A    6/1977    Gruber et al.
(Continued)

FOREIGN PATENT DOCUMENTS

DE    2039329    5/1971
DE    2451342    5/1976
(Continued)

OTHER PUBLICATIONS

International Search Report for PCT/DE2012/100262, published Jun. 27, 2013.
(Continued)

*Primary Examiner* — Tam M Nguyen
(74) *Attorney, Agent, or Firm* — Honigman Miller Schwartz and Cohn LLP; Heidi M. Berven; Jonathan P. O'Brien

(57) ABSTRACT

The invention relates to a method for improving the transportability of heavy crude oil.
Proceeding from the disadvantages of the known prior art a method is to be provided, in which an additive can be used which is producible from a byproduct arising during mineral oil production. The method is to be performable with low expenditure and without any special safety precautions. Further the additive shall lead to an increased yield of conventional petroleum during subsequent refining.
According to the invention, an aqueous hydrocarbon mixture having a chain length of predominantly C4 to C12 which does not contain any oxygen-containing hydrocarbon compounds is utilized. This is produced in the area of a mineral oil field from natural gas arising as by-product and/or mineral oil-associated gas. Thereby from the heavy crude oil a crude oil which is light in quality and transportable is obtained. During the subsequent refining of the light crude oil to give conventional petroleum, the amount of (Continued)

petroleum produced is increased by the amount of hydrocarbons present in the aqueous hydrocarbon mixture.

18 Claims, 2 Drawing Sheets

(56) References Cited

U.S. PATENT DOCUMENTS

| | | |
|---|---|---|
| 4,076,761 A | 2/1978 | Chang et al. |
| 4,481,305 A | 11/1984 | Jorn et al. |
| 7,861,737 B2 | 1/2011 | Henaut |
| 2005/0197412 A1 | 9/2005 | Van Egmond et al. |
| 2009/0014336 A1 | 1/2009 | Olah et al. |

FOREIGN PATENT DOCUMENTS

| | | |
|---|---|---|
| DE | 3609641 | 9/1987 |
| EP | 0164156 | 11/1985 |
| WO | 03020636 | 3/2003 |
| WO | 2009012154 | 1/2009 |
| WO | 2010107929 | 9/2010 |
| WO | 2011006024 | 3/2011 |

OTHER PUBLICATIONS

International Search Report for PCT/DE2013/100302, published Mar. 13, 2014.
Slides from a presentation at a meeting of the National Petrochemical & Refiners Association in San Antonio, TX, in Mar. 2011.
Transcript of a meeting of the Alaska State Legislature House Resources Standing Committee in Anchorage, AK, on Jan. 25, 2012.
Chang, et al., "The Conversion of Methanol and other O-Compounds to Hydrocarbons over Zeolite Catalysts", Journal of Catalysis, vol. 47, No. 2, Jan. 1, 1977 (Jan. 1, 1977).

METHOD FOR IMPROVING THE TRANSPORTABILITY OF HEAVY CRUDE OIL

The invention relates to a method for improving the transportability of heavy crude oil.

It is generally known to transport mineral oil produced in a mineral oil field as crude oil for further processing in a refinery via pipelines, wherein these pipelines can extend over distances of several thousand kilometers.

If only heavy or super heavy crude oils may still be produced in a mineral oil field, that is to say those having a viscosity of less than 40 000 mPa s or 24° API (API=American unit of density for crude oil), for example, then a relatively long transport of such crude oils through pipelines is no longer possible or is uneconomical without additional measures.

Therefore, various possibilities have already been sought for improving the transportability of heavy crude oil, in particular by decreasing the viscosity.

DE 36 09 641 A1 discloses, for the transport of viscous crude oil, to convert it into an oil-in-water emulsion with at least 10 to 15% water with addition of a special emulsifier based on oxethylate.

According to WO 2011/006024 A2, for reducing the viscosity, it is proposed to use a polymer consisting of a nonionic monomer and at least 25 mol % of cationic monomers.

The addition of emulsifiers or polymers as diluent is associated with additional costs and requires that they must be removed again before refining the crude oil.

In DE 2 039 329 A it is proposed to improve transport by heating crude oil to temperatures of 340 to 650° C. However, this is associated with considerable expenditure and is not economically achievable for transport distances of several thousand kilometers.

U.S. Pat. No. 7,861,737 B2 proposes, to improve transport of heavy oil, to add to this first a solvent, such as naphtha, for example, in order to dilute the heavy oil or crude oil. Then, dimethyl ether (DME) in the liquid or gaseous state is introduced under high pressure, at least 4 bar. The addition of DME is said to lead to a marked reduction in viscosity of the heavy oil or crude oil, as a result of which the transportability is improved.

The disadvantage of this solution is that two components, naphtha and DME, must be provided, transported to the mineral oil field and added to the heavy oil or crude oil. The addition of DME as a component having a high partial pressure is associated with additional expenditure on mixing and pumping. Naphtha contains predominantly cycloparaffins. The additives naphtha and DME must be co-separated off by distillation during the following refining of the crude oil. DME is a highly explosive gas under standard conditions. The handling of this high-explosive substance demands considerable safety measures.

The object of the invention is to provide a method for improving the transportability of heavy crude oil by means of an additive which is producible from a by-product arising during mineral oil production, does not demand any special safety precautions, can be added with low expenditure to the heavy crude oil, need not be separated off during the subsequent refining, and leads to an increased yield of conventional petroleum during refining.

According to the invention, the object is achieved by the features specified in claim 1. Advantageous embodiments and developments of the procedure are the subject matter of claims 2 to 18.

According to the invention, there is added to the heavy crude oil, before it is degassed and dewatered, as a viscosity-reducing agent, an aqueous hydrocarbon mixture having a chain length of predominantly C4 to C12 which does not contain any oxygen-containing hydrocarbon compounds and is produced in the area of a mineral oil field from natural gas arising as by-product and/or mineral oil-associated gas.

Predominantly here means that approximately 80 to 85% of the hydrocarbons have a chain length of C4 to C12. The residual 15 to 20% is compounds having chain lengths C3 or >C12, respectively.

The amount of the hydrocarbon mixture used is preferably in the range from 20 to 40%, with respect to the amount of crude oil.

The special hydrocarbon mixture is produced on site as follows:

a) conversion of the natural gas and/or mineral oil-associated gas into a methanol/water mixture,
b) processing of the methanol-water mixture by distillation to form a distillate having a high water and alcohol content of above 90%,
c) catalytic conversion of the distillate into a dimethyl ether/methanol/water mixture,
d) conversion of the dimethyl ether/methanol/water mixture by dehydration into the aqueous hydrocarbon mixture having a chain length C4 to C12.

The hydrocarbon mixture obtained according to method steps a) to d) is added either untreated or after degassing and/or dewatering to the heavy crude oil, as a result of which, from the heavy crude oil, a crude oil light in quality is obtained which is transported via lines to a refinery. During the subsequent refining of the light crude oil to give conventional petroleum, the amount of petroleum produced is increased by the amount of hydrocarbons present in the aqueous hydrocarbon mixture.

The starting product, natural gas and/or mineral oil-associated gas, arises in the production of heavy crude oil in mineral oil fields, e.g. in what is termed cluster extraction. The associated gas is separated off by means of a fluid separation arrangement. To date, it was customary practice to compress back the natural gas or associated gas arising as by-product, or to flare it off.

Firstly, the utilization of the natural gas or associated gas arising as by-product directly at the point of formation is of great economic advantage, and secondly the fact that the heavy crude oil modified to form more free-flowing and transportable crude oil need not be subjected to separate treatment. It can then be further processed in a refinery as with standard light crude oil. "Light crude oil" here is taken to mean those crude oils which have an API of about 30° or greater. During the refining of the light crude oil, a further advantage is established. The added hydrocarbon mixture already contains hydrocarbons in the range C4 to C12, as with conventional petroleum. Accordingly, during the refining of the light crude oil, the amount of petroleum produced increases by approximately the fraction of hydrocarbon mixture added according to the invention.

As a result, in comparison with heavy crude oil, markedly higher sales revenues may be achieved. The expenditure for erecting a plant immediately on site for the chemical conversion of natural gas or mineral oil associated gas into a hydrocarbon mixture is therefore amortized even after a relatively short operating time.

Conversion of the natural gas and/or mineral oil-associated gas into a methanol-water mixture can be performed according to two different procedures:

According to a first variant, the following method steps are provided:
  desulfurization; saturation with process condensate and steam;
  pre-cracking into a gas mixture of methane, carbon dioxide and carbon monoxide;
  then, the pre-cracked gas mixture is catalytically converted into synthesis gas at elevated temperature and a pressure of at least 50 bar in an autothermal reactor with addition of preheated oxygen, which synthesis gas is cooled and compressed by means of a compressor, and
  then, therefrom, by catalytic conversion in the context of a two-stage water-methanol synthesis in a water-cooled and in a gas-cooled reactor, methanol is produced and by subsequent multi-stage condensation crude methanol (methanol-water mixture) is obtained.

According to a second variant, the following method steps are provided:
  desulfurization; saturation with process condensate and steam;
  subsequent diverting of a substream of water-saturated process gas which is precracked into a gas mixture of methane, hydrogen, carbon dioxide and carbon monoxide;
  this gas mixture is converted in a steam reformer into a first synthesis gas, a mixture of hydrogen, carbon dioxide and carbon monoxide, which is reintroduced to the water-saturated process gas stream and mixed therewith;
  then, the process gas stream is catalytically converted at elevated temperature and a pressure of at least 50 bar in an autothermal reactor with addition of preheated oxygen into a second synthesis gas which is cooled and compressed by means of a compressor, and
  then, therefrom, by catalytic conversion in the context of a two-stage water-methanol synthesis, in a water-cooled and in a gas-cooled reactor, methanol is produced and by subsequent multi-stage condensation, crude methanol (methanol-water mixture) is obtained.

The methanol-water mixture (crude methanol) obtained in each case is subsequently subjected to a two-stage distillation, wherein, in the first stage, low-boiling compounds are separated off, and in the second stage higher-boiling compounds are separated off, and a distillate having a high water and alcohol content is formed. This is then catalytically converted in a fixed-bed reactor into a dimethyl ether/methanol/water mixture which is then converted in further adiabatically operating reactors in the temperature range from 300 to 450° C. into the aqueous hydrocarbon mixture as end product.

This hydrocarbon mixture has, for example, the following composition:
  57% water
  5% propane
  38% hydrocarbons (principally in the range C4 to C12).

The hydrocarbons consist of paraffins, olefins and aromatics.

The dimethyl ether/methanol/water mixture arising in the fixed-bed reactor is preferably admixed with recycled gas for temperature adjustment.

According to a preferred embodiment, a first subquantity of synthesis gas is diverted, run in a cycle, and during this compressed to the required operating pressure.

A second subquantity of synthesis gas can further be diverted, from which second subquantity, in a pressure-swing system, hydrogen is separated off which is reintroduced into the synthesis gas stream on the suction side of the compressor.

The hydrocarbon mixture that is produced directly at the extraction site is then, either untreated, or after degassing and/or dewatering, added to the heavy crude oil, wherein this is diluted and as a result the transportability is markedly improved.

Via the amount added of hydrocarbon mixture, the viscosity may be appropriately adjusted to the desired transport quality in a targeted manner. To decrease the viscosity of the heavy crude oil, depending on the API degree, up to 40%, with respect to the amount of heavy crude oil, is added. As a result, a dilution sufficiently high for transport is achieved.

Larger amounts can also be added, but they only have an unsubstantial effect on further reduction in viscosity. Even small amounts added, in the single-figure percentage range, can be sufficient in order to improve the quality of the heavy crude oil. Preferably, at least 10%, with respect to the amount of unpurified crude oil, lead to very good results.

To the heavy crude oil is added a hydrocarbon mixture having a chain length of predominantly C4 to C12 which does not contain any oxygen-containing hydrocarbon compounds.

The special conditions for obtaining this hydrocarbon mixture are stated in the exemplary embodiment hereinafter.

The methanol formed as an intermediate product should preferably still have a residual water content of at least 4%, and an alcohol content of 0.1%. It is catalytically converted by dehydration to an aqueous and gas-containing hydrocarbon mixture.

This hydrocarbon mixture can, in the area of the mineral oil field, be fed directly for improvement of transportability either to the heavy crude oil already produced and/or via the borehole to the heavy crude oil still stored under ground.

Preferably, the introduction into a borehole proceeds via a purge tube inserted therein.

In individual shafts for extraction of a mineral oil cluster, there is also the possibility that a first subquantity of hydrocarbon mixture is fed above the borehole in order to improve the transportability of the heavy crude oil. The mineral oil shafts of a cluster are combined, wherein, after the combining, the fluid streams are mixed, and in a mass separation arrangement, water and oil-associated gas are separated off. During the mixing, again, an appropriate amount of hydrocarbon mixture can be added. This is metered, in dependence on the viscosity of the heavy oil in such a manner that the transportability thereof is improved in a sufficient extent to a quality such as light crude oil.

If necessary, the hydrocarbon mixture formed, before it is contacted with the heavy crude oil, can be further purified, that is to say dewatered and degassed.

By separate water removal and degassing, from the aqueous hydrocarbon mixture, a water-free hydrocarbon mixture can be generated.

In principle, the treated hydrocarbon mixture can be added at any desired point for improving the extractability or transportability.

Purified hydrocarbon mixture can preferably be fed on the suction side of the pump used for transport of the crude oil. Optionally, hydrocarbon mixture and heavy crude oil can also be mixed in a separate mixing arrangement to give light crude oil.

Usage rates of hydrocarbon mixture of approximately 20% are already sufficient in order to convert e.g. heavy oil (API 23°) to light crude oil (API 31°).

Preferably, the viscosity of the extracted heavy crude oil is measured and, depending on the current measurement result, the amount of hydrocarbon mixture is added in a metered manner in order to obtain light crude oil.

Untreated hydrocarbon mixture must be added to the heavy crude oil within the extraction and transport route of the heavy crude oil before the mass separation arrangement is reached. In contrast, treated hydrocarbon mixture which is dewatered and degassed can be added to the heavy crude oil at all points of the extraction and transport route.

The invention is described in more detail hereinafter with two examples.

In the associated drawing.

In a mineral oil field, 1088 t/h of heavy crude oil (API 23°) are extracted which has the following composition:

| hydrocarbons | 818 t |
|---|---|
| water | 240 t and |
| gaseous components | 30 t. |

Figure 1:
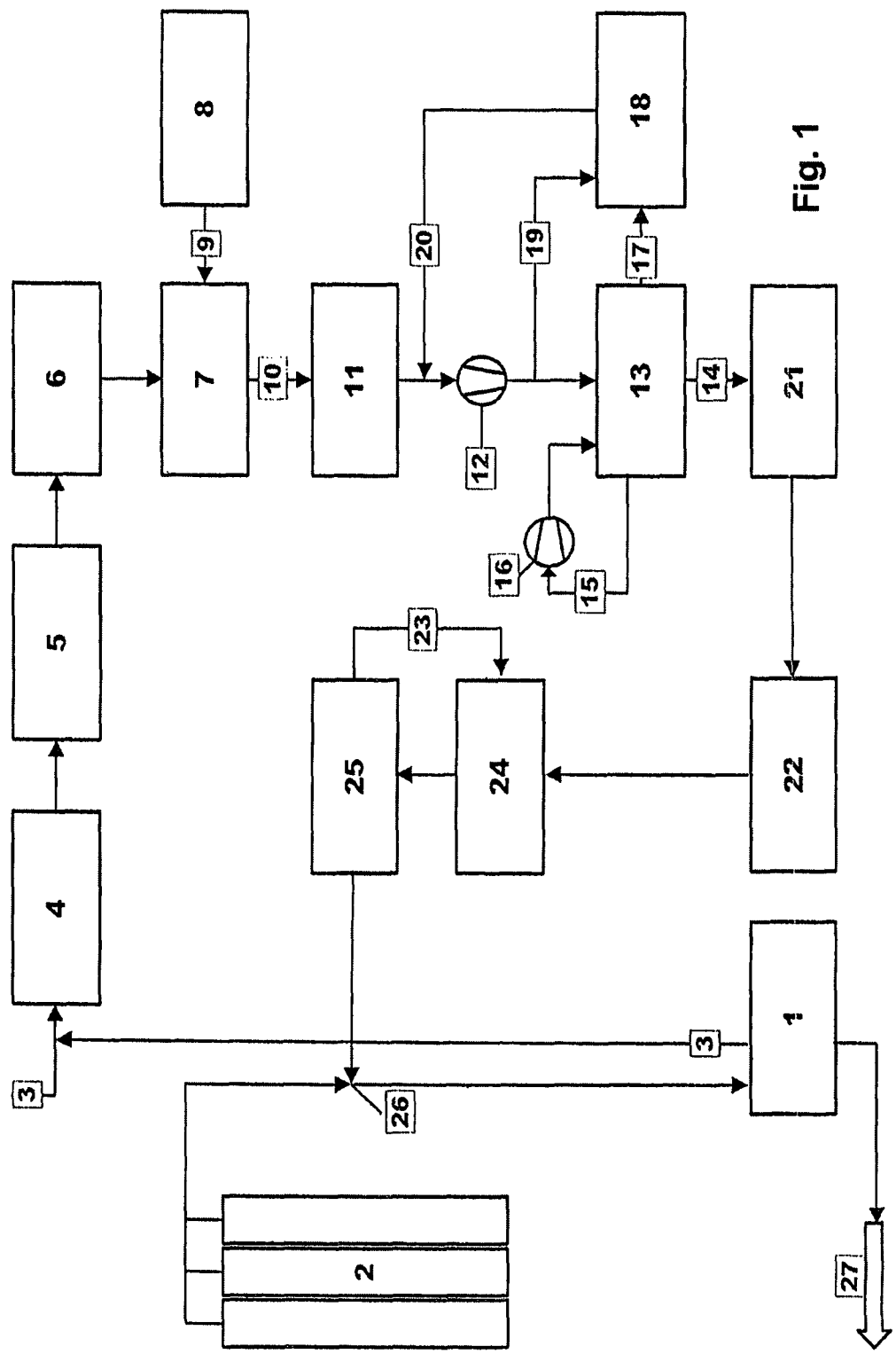
FIG. 1 shows a first variant embodiment as a flowchart.
Figure 2:
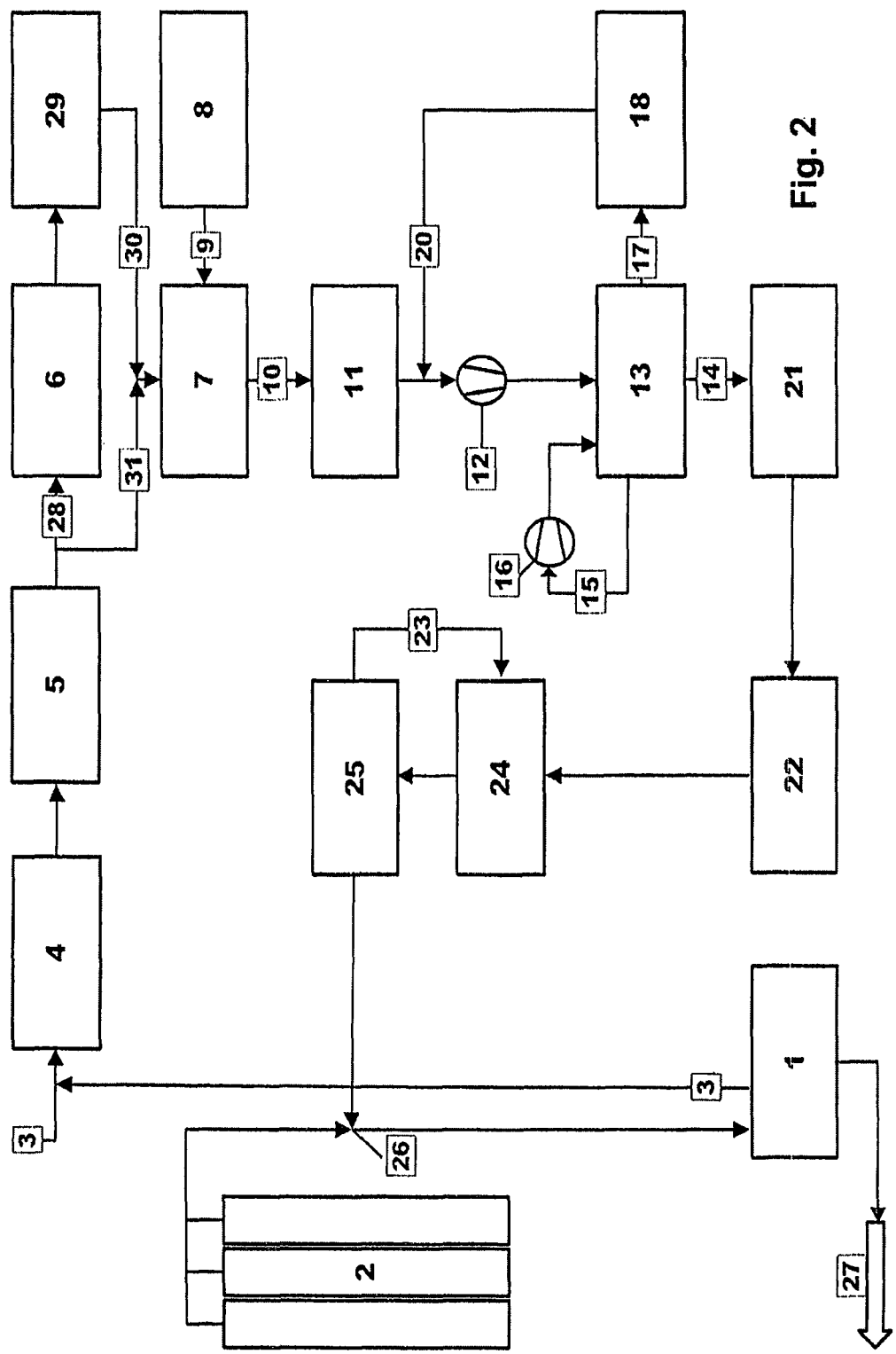
FIG. 2 shows a second variant embodiment as a flowchart.

In a central oil processing facility 1, the crude oil originating from differing boreholes 2 is combined, mixed, and then fed to a separating arrangement, in which the aqueous phase and the gaseous components are separated off. The separating arrangement is a component of the central oil processing facility 1. In FIGS. 1 and 2, three boreholes 2 are shown symbolically.

In connection with mineral oil extraction, natural gas/mineral oil-associated gas arises having the following composition:

| nitrogen | 1.5% |
|---|---|
| methane | 92% |
| ethane | 3.5% |
| propane | 1.5% |
| higher hydrocarbons | 1% |
| sulfur | 50 ppm. |

The natural gas/oil-associated gas (350 000 m$^3$ (standard cubic meters)/h) is converted as follows into a hydrocarbon mixture in a chemical plant erected on the site of the mineral oil field.

EXAMPLE 1

As shown in FIG. 1, natural gas/oil-associated gas 3 is first desulfurized at a pressure of 70 bar at a temperature of 375° C. over a zinc oxide bed (desulfurization unit 4), thereafter saturated with process condensate and steam (saturator 5) and after establishing a steam/carbon ratio of 1.0 in the prereformer 6, an adiabatically operating catalytic reactor, is precracked at 480° C. into a mixture of methane, carbon dioxide and carbon monoxide.

After further heating to 630 to 650° C., the precracked gas is fed to an autothermal reformer 7. In this catalytic reactor, by addition of oxygen 9 that is preheated to 230° C. and which is obtained in an air separation unit 8, a synthesis gas 10 is generated at 1030° C., which synthesis gas consists of hydrogen, carbon monoxide and carbon dioxide, and contains only a very small amount of uncracked methane. This synthesis gas is cooled in a waste-heat system 11.

Via various stages which are used for steam generation and/or heating of various gas/product streams, the now cooled synthesis gas at 55 bar is compressed by a compressor 12 to 75 bar. Then in a dual system, consisting of a water-cooled and a gas-cooled reactor 13, synthesis gas is catalytically converted in the temperature range from 220 to 260° C. to methanol and by condensation a crude methanol 14 having the following composition is obtained:

| methanol | 83% by weight |
|---|---|
| carbon dioxide | 3.6% by weight |
| water | 11.7% by weight |
| methane | 1.5% by weight |
| higher hydrocarbons | 0.1% by weight |
| higher alcohols | 0.1%. |

During the methanol synthesis, a subquantity of synthesis gas is run in a cycle via a circuit line 15 and during this, by means of a further compressor 16, brought to the required pressure. On account of the impurities present in the synthesis gas, a subquantity of synthesis gas is diverted as purge gas 17 and run via a pressure-swing arrangement (PSA) 18. To this PSA a synthesis gas substream 19 is also fed at high pressure, which synthesis gas substream 19 is branched off after the pressure elevation by means of the compressor 12. The hydrogen 20 generated in the PSA 18 is returned to the synthesis gas stream on the suction side of the synthesis gas compressor 12.

The crude methanol 14 that is condensed in a plurality of stages after the methanol synthesis is first degassed in a distillation unit 21 downstream from the methanol synthesis and then purified to remove low-boiling products and finally higher-boiling products. Compared with the classical three-stage distillation for producing marketable methanol, the distillation is carried out in the temperature range from 70 to 140° C. in only two columns, and a residual water content of 4% in the methanol generated is established. Overall, after the distillation, 435 t/h of crude methanol arise, which contain 17 t of water.

The methanol distilled to 4% water content is then catalytically converted into a DME (dimethyl ether)/methanol/water mixture in a fixed bed reactor 22 (DME reactor). The reaction product from the DME reactor is admixed with recycle gas 23 for temperature adjustment and then converted in further adiabatically operating reactors 24 in the temperature range from 320 to 420° C. to a hydrocarbon/water mixture. From the 435 t/h of methanol used, in this case 191 t of hydrocarbons and 244 t of water are formed. This aqueous hydrocarbon mixture is finally degassed in a degassing unit 25 and added to the untreated heavy crude oil.

According to this example, 435 t of aqueous hydrocarbon mixture having a chain length of predominantly C4 to C12 and not containing any oxygen-containing hydrocarbon compounds are admixed continuously per hour to the untreated heavy crude oil (1088 t/h). In the flowchart, the point of admixture is indicated by the reference sign 26.

The hydrocarbon mixture is admixed before the crude oil/mineral oil-associated gas separation process which takes place within the central oil processing facility 1.

Then the aqueous phase and gaseous components still present, such as nitrogen, carbon dioxide, methane and ethane, are separated off from the diluted crude oil mixture in the central oil processing facility 1. 1004 t/h of treated crude oil having an API 36° are obtained. This can then be transported with pumping stations in conventional transport pipelines 27 over thousands of kilometers without problems. This modified crude oil has a quality such as light crude oil.

The advantage of the further processing or refining of the light crude oil to petroleum is that the special hydrocarbons added to improve the transportability have absolutely no disadvantage on the refining process and become an active component of the petroleum produced, as a result of which the amount of petroleum produced is increased by this share.

EXAMPLE 2

The variant embodiment shown in FIG. 2 differs from the embodiment shown in FIG. 1 in the following process steps.

After the saturator 5, via a first line 28, a first substream (quantitative share about 40%) of the water-saturated desulfurized process gas is mixed with stream and fed at a temperature of about 480° C. to the prereformer 6.

Therein, the process gas is precracked into a mixture of methane, carbon dioxide, hydrogen and carbon monoxide. After further heating up to 520° C., the precracked process gas arrives in a steam reformer 29, an externally heated tube reactor having a nickel catalyst, and is converted therein into a first synthesis gas 30, a mixture of hydrogen, CO and $CO_2$. This first synthesis gas 30 is returned to the substream (share approximately 60%) conducted in the other, second line 31 of the water-saturated desulfurized process gas, which arises downstream of the saturator 5, mixed therewith, and fed at a mixture temperature of 670° C. to the autothermal reformer 7.

The division of the process gas into two substreams can be performed either upstream or downstream of the saturator 7, or downstream of the prereformer 6.

In the autothermal reformer 7, an adiabatically operating catalytic reactor, the mixed gas, by addition of oxygen 9 heated to 240° C. which oxygen 9 is obtained in an air separation arrangement 8, is completely converted at 980° C. to a second synthesis gas 10' which only contains a very small amount of uncracked methane. This synthesis gas is cooled in the downstream waste-heat system 11.

The synthesis gas present at a pressure of 32 bar is then further treated in a manner analogous to that stated in example 1, in order to produce an aqueous hydrocarbon mixture having a chain length of predominantly C4 to C12, with the sole difference that, downstream of the compressor 12, no synthesis gas substream 19 is branched off and fed to the pressure-swing arrangement (PSA) 18.

With this method variant, it is possible, compared with the procedure according to example 1, to reduce the gas consumption for production of the aqueous hydrocarbon mixture by approximately 10%.

The invention claimed is:

1. A method for improving the transportability of heavy crude oil from a mineral oil field to a refinery, wherein a viscosity-reducing agent is added to the heavy crude oil, characterized in that the viscosity-reducing agent is an aqueous hydrocarbon mixture having a chain length of predominantly C4 to C12, which does not contain any oxygen-containing hydrocarbon compounds, and is produced on the site of the mineral oil field from arising natural gas and/or mineral oil-associated gas using the following method steps:
   a) conversion of the natural gas and/or mineral oil-associated gas into a methanol/water mixture,
   b) processing of the methanol-water mixture by distillation to form a distillate having a high water and alcohol content of above 90%,
   c) catalytic conversion of the distillate into a dimethyl ether/methanol/water mixture,
   d) conversion of the dimethyl ether/methanol/water mixture by dehydration into the aqueous hydrocarbon mixture having a chain length of predominantly C4 to C12;

and the hydrocarbon mixture obtained according to method steps a) to d) is added either untreated or after degassing and/or dewatering to the heavy crude oil, as a result of which, from the heavy crude oil, a crude oil light in quality is obtained which is transported via lines to a refinery and during the subsequent refining of the light crude oil to give conventional petroleum, the amount of petroleum produced is increased by the hydrocarbons present in the aqueous hydrocarbon mixture.

2. The method as claimed in claim 1, characterized in that the conversion of the natural gas and/or mineral oil-associated gas into a methanol-water mixture is performed on the site of the mineral oil field with the following method steps:
   desulfurization;
   saturation with process condensate and steam;
   pre-cracking into a gas mixture of methane, carbon dioxide and carbon monoxide;
   then, the pre-cracked gas mixture is catalytically converted into synthesis gas at elevated temperature and a pressure of at least 50 bar in an autothermal reactor with addition of preheated oxygen, which synthesis gas is cooled and compressed by means of a compressor, and
   then, therefrom, by catalytic conversion in the context of a two-stage methanol synthesis in a water-cooled and in a gas-cooled reactor, methanol is produced and by subsequent multi-stage condensation crude methanol (methanol-water mixture) is obtained.

3. The method as claimed in claim 1, characterized in that the conversion of the natural gas and/or mineral oil-associated gas into a methanol-water mixture is performed on the site of the mineral oil field by means of the following method steps:
   desulfurization;
   saturation with process condensate and steam;
   subsequent diverting of a substream of water-saturated process gas which is precracked into a gas mixture of methane, hydrogen, carbon dioxide and carbon monoxide;
   this gas mixture is converted in a steam reformer into a first synthesis gas, a mixture of hydrogen, carbon dioxide and carbon monoxide, which is reintroduced to the water-saturated process gas stream and mixed therewith;
   then, the process gas stream is catalytically converted at elevated temperature and a pressure of at least 50 bar in an autothermal reactor with addition of preheated oxygen into a second synthesis gas which is cooled and compressed by means of a compressor, and
   then, therefrom, by catalytic conversion in the context of a two-stage methanol synthesis, in a water-cooled and in a gas-cooled reactor, methanol is produced and by subsequent multi-stage condensation, crude methanol (methanol-water mixture) is obtained.

4. The method as claimed in claim 3, characterized in that the water-saturated process gas, after the pre-reformer, is divided into two substreams, wherein the one substream is run to the steam reformer and the other substream is run to the autothermal reformer.

5. The method as claimed in claim 4, characterized in that the methanol-water mixture (crude methanol) obtained is subjected to a two-stage distillation, wherein, in the first stage, low-boiling compounds are separated off, and in the second stage higher-boiling compounds are separated off, and a distillate having a high water and alcohol content is formed, which is then catalytically converted in a fixed-bed reactor into a dimethyl ether/methanol/water mixture which is then converted in further adiabatically operating reactors in the temperature range from 300 to 450° C. into the aqueous hydrocarbon mixture as end product.

6. The method as claimed in claim 5, characterized in that a methanol having a residual water content of at least 4%, and an alcohol content of 0.1%, is formed as intermediate product.

7. The method as claimed in claim 6, characterized in that the dimethyl ether/methanol/water mixture arising in the fixed-bed reactor is admixed with recycled gas for temperature adjustment.

8. The method as claimed in claim 7, characterized in that a first subquantity of synthesis gas is diverted, run in a cycle, and during this compressed to the required operating pressure.

9. The method as claimed in claim 8, characterized in that a second subquantity of synthesis gas is diverted, hydrogen is separated off in a pressure-swing appliance, which hydrogen is introduced into the synthesis gas stream on the suction side of the compressor.

10. The method as claimed in claim 9, characterized in that the hydrocarbon mixture formed is fed directly on the site of the mineral oil field either to the heavy crude oil already produced and/or via the borehole to the heavy crude oil still stored under ground.

11. The method as claimed in claim 10, characterized in that the hydrocarbon mixture formed is introduced into the borehole via a purge tube.

12. The method as claimed in claim 10, characterized in that the hydrocarbon mixture formed is dewatered and degassed before it is contacted with the heavy crude oil.

13. The method as claimed in claim 12, characterized in that treated hydrocarbon mixture that is dewatered and degassed is added to the heavy crude oil before or after the central oil processing facility.

14. The method as claimed in claim 12 characterized in that non-treated hydrocarbon mixture is added to the heavy crude oil before the central oil processing facility.

15. The method as claimed in claim 14, characterized in that, after separating off water and oil-associated gas from the crude oil, a further amount of treated hydrocarbon mixture is added to the crude oil, which, depending on the viscosity of the heavy oil, is metered in such a manner that a light crude oil is formed.

16. The method as claimed in claim 15, characterized in that treated hydrocarbon mixture is fed on the suction side of the pump used for the transport of the crude oil.

17. The method as claimed in claim 16, characterized in that the viscosity of the extracted heavy crude oil is measured, and, depending on the current measurement result, the amount of hydrocarbon mixture is added in a metered manner in order to obtain light crude oil.

18. The method as claimed in claim 17, characterized in that treated hydrocarbon mixture and heavy crude oil are mixed in a separate mixing arrangement.

* * * * *